United States Patent [19]

Haas et al.

[11] Patent Number: 5,750,679
[45] Date of Patent: May 12, 1998

[54] PROCESS FOR OBTAINING PHARMACOLOGICALLY ACTIVE COMPOUNDS FROM COMPLEX MIXTURES OF SUBSTANCES

[75] Inventors: Peter Haas; Heinz Engelhardt, both of Saarbrücken; Stefan Müllner, Hochheim, all of Germany

[73] Assignee: Hoechst Aktiengesellschaft, Frankfurt am Main, Germany

[21] Appl. No.: 294,803

[22] Filed: Aug. 25, 1994

[30] Foreign Application Priority Data

Aug. 27, 1993 [DE] Germany ............... 43 28 799.9

[51] Int. Cl.⁶ ............... C07H 1/00; B01D 11/04; C07D 305/00; C07C 27/10
[52] U.S. Cl. ............... 536/127; 422/256; 536/1.11; 536/4.1; 536/115; 536/124; 549/231; 552/502; 562/869; 568/700
[58] Field of Search ............... 210/634, 198.2, 210/656; 536/127, 1.11, 4.1, 115, 124; 422/256; 549/231; 552/502; 562/869; 568/700

[56] References Cited

U.S. PATENT DOCUMENTS

| | | | |
|---|---|---|---|
| 4,550,198 | 10/1985 | Myerson | 560/486 |
| 4,956,052 | 9/1990 | Hirata et al. | 203/19 |
| 5,252,729 | 10/1993 | Decrosta et al. | 540/18 |
| 5,340,475 | 8/1994 | Cortes et al. | 210/198.2 |

OTHER PUBLICATIONS

J.W. Hills et al., "Simultaneous Supercritical Fluid Derivatization and Extraction," Analytical Chemistry, Bd. 63, No. 19, pp. 2152–2155 (Oct. 1991).

L.Q. Xie et al., "Biomedical Applications of Analytical Supercritical Fluid Separation Techniques," Analytical Biochemistry, Bd. 200, No. 1, pp. 7–19 (Jan. 1992).

K.D.R. Setchell et al., "General Methods for the Analysis of Metabolic Profiles of Bile Acids and Related Compounds in Feces," J. of Lipid Research, Bd. 24, No. 8, pp. 1085–1100 (Aug. 1983).

*Primary Examiner*—Elli Peselev
*Attorney, Agent, or Firm*—Finnegan, Henderson, Farabow, Garrett & Dunner, L.L.P.

[57] ABSTRACT

A process for obtaining pharmacologically active compounds from complex mixtures of substances Free organic acids, hydroxy acids, fatty alcohols, sugars and hydroxy-substituted steroids are obtained from complex mixtures of substances by mixing the material to be extracted with a polar solvent, drying the resulting mixture, subsequently silylating, esterifying or acylating, and extracting the resulting material with a supercritical fluid under a pressure of more than 200 bar.

7 Claims, No Drawings

PROCESS FOR OBTAINING PHARMACOLOGICALLY ACTIVE COMPOUNDS FROM COMPLEX MIXTURES OF SUBSTANCES

The detection and recovery of pharmacologically active compounds and their metabolites in biological matrices often involves great problems because extractions with organic solvents or solvent mixtures and/or wet chemical methods are, as a rule, time-consuming and not quantitative. In addition, account must be taken of the consumption, which is usually not negligible, of organic solvents. Moreover, the sample preparation method cannot in most cases be coupled on-line to the analytical method.

The said disadvantages prevent widespread use of such methods in clinical diagnosis owing to the lack of a simple and reproducible analytical method. The main problem with this is less the separation than the sample preparation which is elaborate and therefore has low reproducibility. Improvements can be achieved only by use of selective extraction methods.

A suitable alternative for the sample preparation is extraction with supercritical fluids (SFE) because it does not have the abovementioned disadvantages. However, in most cases the metabolites of interest are too polar for direct extraction by SFE, or isolating from complex mixtures of substances is particularly time consuming (K. D. R. Setchell et al., J. of Lipid Research, Vol. 24, (1983), pages 1085–1100). In the body, pharmaceuticals and xenobiotics are, as a rule, transformed by the liver into more polar metabolites, for example into alcohols, carboxylic acids, glucuronides or sulfates, in order to facilitate excretion.

The object of the present invention was to develop a process for the extraction and analysis of free organic acids and hydroxy acids, fatty alcohols, sugars and hydroxy-substituted steroids and esters of the aforementioned compounds from complex mixtures of substances, in which the extraction is essentially complete.

A process by which free organic acids and hydroxy acids, fatty alcohols, sugars and hydroxy-substituted steroids and their esters can be obtained essentially completely from complex mixtures of substances has now been found and comprises A) mixing the material to be extracted with a polar solvent or a mixture of polar solvents, and concentrating the resulting mixture to dryness, B) silylating, esterifying or acylating the material obtained from A) and C) extracting the material obtained from B) with a supercritical fluid under a pressure of more than 200 bar.

Examples of complex mixtures of substances are urine, parenchymal tissue, feces or serum from animals or humans, which can be mechanically comminuted, lyophilized or extracted.

Examples of suitable mixtures of polar solvents are methanol/water in the ratio 2:1 by volume, methanol/water/heptane in the ratio 1:1:0.5 by volume or solvent mixtures with comparable polarity.

The type of derivatization essentially depends on the analytical method used after the extraction. The methods which can be used for analysis with the aid of gas chromatography (GC) are silylation, for example with hexamethyldisilazane (HMDS) and trimethylchlorosilane (TMCS), or esterification, for example with boron trifluoride in methanol, or acylation, for example with p-dimethylaminopyridine/acetic anhydride.

The term supercritical fluid stands for, for example, $CO_2$, $N_2O$, n-butane, n-pentane or $C_1$-chlorofluorocarbons, preferably for $CO_2$.

Suitable compounds which can be extracted according to the invention are:

A) free organic acids, for example aromatic or aliphatic carboxylic acids such as caproic acid, valeric acid, adipic acid, glutaric acid, indolecarboxylic acid or β-phenylpropanoic acid, in particular saturated or unsaturated fatty acids, preferably higher fatty acids with 12 to 18 carbon atoms such as capric, lauric, myristic, palmitic or stearic acid, preferably myristic, palmitic, stearic, oleic and linoleic acids;

B) hydroxy acids, for example lower mono-, di- or polyhydroxy carboxylic acids such as lactic, malic, tartaric or citric acid, but also hydroxy fatty acids such as ricinoleic acid or aromatic acids such as salicylic acid;

C) fatty alcohols, which can be saturated or unsaturated, for example those with 12 to 18 carbon atoms, for example myristyl, cetyl, stearyl or oleyl alcohol;

D) sugars, for example monosaccharides, for example glucose, mannose, fructose, or disaccharides, for example sucrose or lactose, with the monosaccharides being preferred;

E) hydroxy-substituted steroids, for example cholic acid, chenodeoxycholic acid, deoxycholic acid, ursodeoxycholic acid, lithocholic acid, pregnanetriol, cholesterol, cholesterol esters, for example coprosterol, β-sitosterol, but especially the bile acids such as cholic acid, lithocholic acid, deoxycholic acid and ursodeoxycholic acid.

Examples which may be mentioned of esters which can be extracted according to the invention are those with lower alcohols, especially the methyl ester, and the silyl esters obtained by derivatization, preferably the TMS esters obtained with trimethylchlorosilane.

Compounds which are particularly preferred according to the invention from those mentioned above are the higher fatty acids, monosaccharides, bile acids and cholesterol, especially the bile acids.

Extraction of bile acids from biological matrices has to date represented a great problem because bile acids not only display amphophilic behavior, high polarity and a tendency to self-association but also have high binding affinities for serum proteins or particular polysaccharides from vegetable fibers. These properties of the bile acids make extraction from feces or serum difficult by conventional methods. It has been possible to overcome these extraction problems according to the invention.

The procedure for process step A) is as follows:

The material to be analyzed, for example rat feces, is mixed with a solvent mixture, for example methanol/water in the ratio 2:1 by volume, and stirred at room temperature. Coarse material is, where appropriate, comminuted to a particle size of about 0.2 mm before or after the stirring in the methanol/water mixture. For analysis of cholesterol esters, fatty acids or fatty alcohols it is beneficial to add a solvent which is immiscible with polar solvents, for example n-heptane. The material is subsequently concentrated under reduced pressure, preferably to dryness.

The material obtained from process step A) is derivatized in process step B) by known methods. If the material is to be analyzed with the aid of gas chromatography, the derivatization takes place by silylation or acylation.

In the silylation, the material derived from A) is taken up, for example in pyridine, and stirred with hexamethyldisilazane (HMDS) and trimethylchlorosilane (TMCS) at 25° C. for about 15 min and then concentrated under reduced pressure until the material is free-flowing. This should be done at temperatures below 50° C.

The methods used both for an esterification and for the acylation should do without acid catalysis, such as, for example, boron trifluoride in methanol. It is subsequently possible to silylate as shown above or, for example, acylate with p-dimethylaminopyridine/acetic anhydride.

The material obtained from process step B) is extracted with a supercritical fluid. The preferred fluid is $CO_2$, which is used under a pressure of more than 200 bar, preferably 430 to 480 bar. The extraction takes place at temperatures from 30° to 50° C., preferably 35° to 40° C., for 1 to 4 hours, preferably 2 to 3 hours. It is possible where appropriate also to add to the carbon dioxide 5 to 10% of polar additives such as, for example, methanol, ethanol or acetone, or n-heptane during the extraction.

The resulting extract is prepared for the GC analysis by known methods. In the case of silylation, subsequent treatment of the extract with pyridine, HMDS and TMCS has proven appropriate.

The construction and the mode of functioning of the SFE apparatus are simple. Liquid $CO_2$ under the pressure necessary for the particular extraction is pumped by a pump, for which it is possible to use both HPLC pumps and long-stroke piston pumps, through an extraction chamber which is located in an oven heated to the extraction temperature and which contains the sample. In this case the extractant attains the supercritical state only on entry into the oven. Downstream of the extraction chamber there is a restrictor which, as flow resistance, has the task of maintaining the extraction pressure in the chamber at moderately high flow rates.

The end of the restrictor is led out of the oven and immersed in a collecting vessel which contains a solvent suitable for the analytes to be extracted. It is worthwhile to cool this receiver when extracting volatile components.

A detailed description of the SFE and GC apparatuses used for carrying out the process according to the invention is given hereinafter.

SFE: Suprex (Pittsburgh, Pa., USA) model SFE/50 steel tubes (12 cm×7 mm i.d.) which are connected with Swagelok fittings (1/16 inch outlets) are used as extraction chamber, n-heptane was admixed with the aid of an HPLC pump, Kontron (Munich, D) model 420, through a 1/16 inch T-piece located upstream of the chamber, quartz glass capillaries (8 m×75 μm i.d.), Microquartz (Munich, D), are used as restrictors, a 10 ml long-neck volumetric flask containing about 5 ml of n-heptane is used as receiver, the carbon dioxide of purity 4.5 was purchased from Messer Griesheim (Saarbrücken, D).

GC: Carlo Erba (Milan, I) model HRGC 5300 Column: DB-5, 15 m×250 μm i.d., df=0.25 μm, J & W Scientific (Folsom, Calif., USA) Injection: 1 μl, split 20:1; carrier gas: $N_2$, 42.3 cm/s; detection: FID The following retention ranges and retention times were found for compounds extracted according to the invention in the column described above under the conditions mentioned there with the following temperature program: 2 min at 50° C., to 170° C. at 20° C./min, to 280° C. at 10° C./min, to 310° C. at 2° C./min, 5 min at 310° C. The accuracy of the retention times is about ±0.05 min.

| Compound class | Retention range/min |
| --- | --- |
| Silanes, siloxanes | 2–8 |
| Monosaccharides | 8–15 |
| Fatty acids and their TMS esters | 15–19 |
| Steroids, general | 26–34 |
| Bile acids, specific | 30–33 |
| Cholesterol esters | >36 |

| Compound | Retention time/min |
| --- | --- |
| β-Phenylpropanoic acid | 8.6 |
| β-Phenylpropanoic acid, TMS ester | 10.35 |
| Myristic acid, TMS ester | 14.4 |
| Indolecarboxylic acid, TMS ester | 15.15 |
| Myristic acid | 15.65 |
| Palmitic acid, TMS ester | 16.4 |
| Palmitic acid | 17.5 |
| Linoleic acid, TMS ester | 18.0 |
| Oleic acid, TMS ester | 18.05 |
| Stearic acid, TMS ester | 18.2 |
| Stearic acid | 19.2 |
| Coprosterol (TMS) | 27.7 |
| Cholesterol | 28.6 |
| Cholesterol (TMS) | 29.25 |
| Lithocholic acid (TMS)$_4$ | 31.0 |
| β-Sitosterol | 31.3 |
| Deoxycholic acid (TMS)$_4$ | 31.95 |
| Cholic acid (TMS)$_4$ | 32.3 |
| Ursodeoxycholic acid (TMS)$_4$ | 32.7 |
| β-Sitosterol (TMS) | 32.75 |

The individual steps in the method are compiled once again in the following table. Whereas extraction and subsequent purification of the extracts takes at least 2 days with conventional methods (K. D. R. Setchell et al., J. Lipid Research, Vol. 24, (1983), pages 1085–1100), the entire sample preparation in the process presented here takes about 4 hours.

| Step | Procedure | Materials | Duration |
| --- | --- | --- | --- |
| Activation | Stirring at room temperature, rotary evaporation | 30 ml of methanol | 45 min |
| Derivatization | Stirring at room temperature, rotary evaporation | 20 ml of pyridine, 2.5 ml of HMDS, 0.8 ml of TMCS | 45 min |
| Extraction | Filling of the extraction chamber, extraction | 80 L of $CO_2$ (g), 15 ml of n-heptane | 2.5 h |

The process according to the invention is described in detail in the following example.

EXAMPLE 1 g of dried rat feces is comminuted to a particle size of about 0.2 mm and stirred in 20 ml of methanol/water (2:1) at 25° C. for 15 min. The mixture is subsequently concentrated under reduced pressure to dryness. The resulting material is mixed with 15 ml of pyridine, 2.5 ml of hexamethyldisilazane (HMDS) and 0.8 ml of trimethylchlorosilane (TMCS), stirred at 25° C. for 15 min and subsequently concentrated under reduced pressure at 40° C. to dryness. The resulting material is extracted with $CO_2$ at 40° C. and 450 bar for 2 hours (Suprex (Pittsburgh, Pa., USA, as described above) model SFE/50 SFE extractor). The receiver comprises about 5 ml of n-heptane in a 10 ml flask. The resulting extract is dried and mixed with 250 μl of pyridine, 150 μl of HMDS and 50 μl of TMCS. After 10 min, a sample can be analyzed in the gas chromatograph (Carlo Erba, Milan, model HRGC 5300). A 1 μl sample is injected into the column described above. Subsequently the following temperature program is carried out:

2 min at 50° C., to 170° C. at 20° C./min, to 280° C. at 10° C./min, to 310° C. at 2° C./min, 5 min at 310° C.

The resulting chromatogram shows complete extraction of β-phenylpropanoic acid; β-phenylpropanoic acid TMS ester; myristic acid TMS ester; myristic acid; palmitic acid TMS ester; palmitic acid; linoleic acid TMS ester; oleic acid TMS ester; stearic acid TMS ester; TMS-coprosterol; TMS-cholesterol; lithocholic acid (TMS)$_4$; β-sitosterol; deoxycholic acid (TMS)$_4$ and TMS-β-sitosterol.

The identity of said compounds is verified by gas chromatography and mass spectroscopy. The completeness of the extraction is proven by another chromatogram.

We claim:

1. A process for obtaining at least one free organic acid, hydroxy acid, fatty alcohol, sugar, hydroxy-substituted steroid, an ester of said free organic acid, an ester of said hydroxy acid, an ester of said fatty alcohol, an ester of said sugar, or an ester of said hydroxy-substituted steroid from a complex mixture comprising at least one of said compounds, which process comprises the steps of:

A) mixing the complex mixture with a polar solvent or a mixture of polar solvents, and concentrating the resulting mixture to dryness;

B) silylating, esterifying or acylating the material obtained from A); and

C) extracting the at least one compound from the material obtained from B) with a supercritical fluid under a pressure of more than 200 bar.

2. The process as claimed in claim 1, wherein $CO_2$ is used as supercritical fluid.

3. The process as claimed in claim 1, wherein a methanol/water mixture in the ratio 2:1 by volume, methanol/water/heptane mixture in the ratio 1:1:0.5 by volume or solvent mixtures with comparable polarity is used as polar solvent.

4. The process as claimed in claim 1, wherein extraction is carried out under a pressure of 430 to 480 bar.

5. The process as claimed in claim 1, wherein fatty acids, monosaccharides, cholesterol or bile acids are extracted.

6. The process as claimed in claim 1, wherein β-phenylpropanoic acid, myristic acid, indolecarboxylic acid, palmitic acid, linoleic acid, oleic acid, stearic acid, coprosterol, cholesterol, lithocholic acid, β-sitosterol, deoxycholic acid, cholic acid, ursodeoxycholic acid or esters of the aforementioned compounds as well as mixtures of the compounds are extracted.

7. The process as claimed in claim 1, wherein silylation is carried out with hexamethyldisilazane or trimethylchlorosilane, esterification is carried out with boron trifluoride in methanol, or acylation is carried out with p-dimethylaminopyridine/acetic anhydride.

* * * * *